United States Patent
Schroeder

[19]

[11] Patent Number: 6,132,469

[45] Date of Patent: Oct. 17, 2000

[54] ACETABULAR LINER EXTRACTOR

[75] Inventor: David W. Schroeder, Winona Lake, Ind.

[73] Assignee: Biomet, Inc., Warsaw, Ind.

[21] Appl. No.: 08/966,314

[22] Filed: Nov. 7, 1997

[51] Int. Cl.$^7$ .......................................................... A61F 2/34
[52] U.S. Cl. ........................ 623/22.24; 606/99; 623/22.28
[58] Field of Search .................................... 606/99, 91, 81, 606/89; 623/22.24, 23.28; 294/95

[56] References Cited

U.S. PATENT DOCUMENTS

| | | |
|---|---|---|
| Re. 28,895 | 7/1976 | Noiles . |
| 1,395,587 | 11/1921 | McLachlan . |
| 2,562,071 | 7/1951 | Stueland . |
| 3,584,318 | 6/1971 | Scales et al. . |
| 3,820,167 | 6/1974 | Sivash . |
| 3,848,272 | 11/1974 | Noiles . |
| 3,859,669 | 1/1975 | Shersher . |
| 3,894,297 | 7/1975 | Mittelmeier et al. . |
| 3,943,576 | 3/1976 | Sivash . |
| 3,971,288 | 7/1976 | Jones et al. . |
| 3,977,026 | 8/1976 | Battault . |
| 4,065,817 | 1/1978 | Branemark et al. . |
| 4,077,070 | 3/1978 | Sivash . |
| 4,172,529 | 10/1979 | D'Errico . |
| 4,180,873 | 1/1980 | Fixel . |
| 4,206,517 | 6/1980 | Pappas et al. . |
| 4,262,369 | 4/1981 | Roux . |
| 4,519,101 | 5/1985 | Schreiber et al. . |
| 4,524,467 | 6/1985 | DeCarlo, Jr. . |

(List continued on next page.)

FOREIGN PATENT DOCUMENTS

| | | |
|---|---|---|
| 0 083 708 | 11/1982 | European Pat. Off. . |
| 0 091 315 | 10/1983 | European Pat. Off. . |
| 0 636 351 A2 | 2/1995 | European Pat. Off. . |
| 2225924 | 11/1974 | France . |
| 2233972 | 1/1975 | France . |
| 2 245 328 | 4/1975 | France . |
| 2 301 217 | 9/1976 | France . |
| 2 315 902 | 1/1977 | France . |
| 2 377 798 | 8/1978 | France . |
| 2 417 972 | 9/1979 | France . |

(List continued on next page.)

OTHER PUBLICATIONS

Booklet entitled "First in the World in Clinical Application The Original Furlong® Hydroxyapatite Ceramic (Osprovit)® Coated Total Hip Replacement", Joint Replacement Instrumentation Ltd., pp. 1–16, Autumn 1987.

"The Original Furlong® Hydroxyapatite Ceramic (Osprovit)® Coated Total Hip Replacement", Furlong® H–A.C. Femoral Stems, Furlong® H–A.C. Threaded Cups, Furlong® H–A.C. Rim Fix Cups, Instrumentation, Joint Replacement Instrumentation Ltd., 2 pages, prior to Nov. 7, 1997.

"The Original Furlong® Hydroxyapatite Ceramic (Osprovit)® Coated Total Hip Replacement", Furlong® H–A.C. Femur Schafte, Furlong® H–A.C. Gewindepfannen, Furlong® H–A.C. Rim–Fix–Pfannen, Instrumentation, Joint Replacement Instrumentation Deutschland GmbH, 2 pages, prior to Nov. 7, 1997.

"The Original Furlong® Hydroxyapatite Ceramic (Osprovit)® Coated Total Hip Replacement", Furlong® Vastagos Femorales H–A.C., Furlong® Copas Roscadas H–A.C., Furlong® Copas Rim Fix H–A.C., Instrumentation, MBA, 2 pages, prior to Nov. 7, 1997.

(List continued on next page.)

Primary Examiner—Bruce Snow
Attorney, Agent, or Firm—Harness, Dickey & Pierce, P.L.C.

[57] ABSTRACT

A preferred embodiment of an extractor employs a pair of arms which laterally move toward each other, thereby applying compressive forces against a first prosthetic component toward a longitudinal centerline. These compressive forces, in combination with longitudinal movement of the arms in relation to a collar of the extractor, serves to easily extract the liner from the shell.

23 Claims, 7 Drawing Sheets

U.S. PATENT DOCUMENTS

| | | | |
|---|---|---|---|
| 4,541,311 | 9/1985 | Trammell, Jr. . | |
| 4,563,778 | 1/1986 | Roche et al. . | |
| 4,596,580 | 6/1986 | Weill . | |
| 4,650,491 | 3/1987 | Parchinski . | |
| 4,676,799 | 6/1987 | Legrand . | |
| 4,678,472 | 7/1987 | Noiles . | |
| 4,686,971 | 8/1987 | Harris et al. . | |
| 4,704,127 | 11/1987 | Averill et al. . | |
| 4,795,469 | 1/1989 | Oh . | |
| 4,795,470 | 1/1989 | Goymann et al. . | |
| 4,813,961 | 3/1989 | Sostegni . | |
| 4,828,565 | 5/1989 | Duthoit et al. . | |
| 4,842,605 | 6/1989 | Sonnerat et al. . | |
| 4,878,916 | 11/1989 | Rhenter et al. . | |
| 4,879,806 | 11/1989 | Feng . | |
| 4,936,855 | 6/1990 | Sherman . | |
| 4,941,700 | 7/1990 | Lin et al. . | |
| 4,964,869 | 10/1990 | Auclair et al. . | |
| 4,969,910 | 11/1990 | Frey et al. . | |
| 4,978,356 | 12/1990 | Noiles . | |
| 4,993,410 | 2/1991 | Kimsey . | |
| 5,002,577 | 3/1991 | Bolesky et al. . | |
| 5,015,257 | 5/1991 | Crowninshield et al. . | |
| 5,041,140 | 8/1991 | Teinturier . | |
| 5,080,678 | 1/1992 | Spotorno et al. . | |
| 5,080,679 | 1/1992 | Pratt et al. . | |
| 5,092,897 | 3/1992 | Forte . | |
| 5,092,898 | 3/1992 | Bekki et al. . | |
| 5,098,437 | 3/1992 | Kashuba et al. . | |
| 5,108,447 | 4/1992 | Zeiler et al. . | |
| 5,112,338 | 5/1992 | Anspach, III . | |
| 5,116,339 | 5/1992 | Glock . | |
| 5,156,606 | 10/1992 | Chin . | |
| 5,171,313 | 12/1992 | Salyer . | |
| 5,181,929 | 1/1993 | Prats et al. . | |
| 5,258,034 | 11/1993 | Furlong et al. . | |
| 5,282,864 | 2/1994 | Noiles et al. . | |
| 5,405,404 | 4/1995 | Gardner et al. . | |
| 5,413,603 | 5/1995 | Noiles et al. . | |
| 5,417,693 | 5/1995 | Sowden et al. | 606/99 |
| 5,431,657 | 7/1995 | Rohr . | |
| 5,571,200 | 11/1996 | Cohen et al. | 623/22 |
| 5,683,399 | 11/1997 | Jones | 606/91 |
| 5,716,401 | 2/1998 | Eberhardt et al. | 606/99 |
| 5,817,096 | 10/1998 | Salyer | 606/81 |
| 5,830,215 | 11/1998 | Incavo et al. . | |
| 5,938,701 | 8/1999 | Hiernard et al. | 623/22 |
| 6,013,082 | 1/2000 | Hiernard et al. . | |

FOREIGN PATENT DOCUMENTS

| | | |
|---|---|---|
| 2 597 329 | 10/1987 | France . |
| 2 598 609 | 11/1987 | France . |
| 2 622 432 | 5/1989 | France . |
| 2 628 967 | 9/1989 | France . |
| 2 631 542 | 11/1989 | France . |
| 29 25 089 A1 | 1/1980 | Germany . |
| 34 46 048 A1 | 10/1985 | Germany . |
| 42 15 888 A1 | 11/1993 | Germany . |
| 1 7117 867 A1 | 5/1989 | U.S.S.R. . |
| 1126961 | 9/1968 | United Kingdom . |
| 1 483 938 | 8/1977 | United Kingdom . |
| 2 117 646 | 10/1983 | United Kingdom . |
| 2 197 204 | 8/1990 | United Kingdom . |
| WO 89/07917 | 9/1989 | WIPO . |
| WO 93/16662 | 9/1993 | WIPO . |

OTHER PUBLICATIONS

Booklet entitled "Prostheses and Instrumentation, The Furlong® H–A.C. Total Hip Replacement", pp. 1–12, Joint Replacement Instrumentation Ltd., Sep. 1985.

"Clinical Orthopaedics and Related Research™", No. Two Hundred Eighty–Two, Role of Ceramic Implants Design & Clinical Success with Total Hip Prosthetic Ceramic–to–Ceramic Bearings, Ian C. Clarke, pp. 19–30, Sep. 1992.

Journal of Biomedical Materials Research, vol. 22, 1988, "The Use of Dense Alumina–Alumina Ceramic Combination in Total Hip Replacement", P. Boutin, P. Christel, J–M. Dorlot, A. Meunier, A. de Roquancourt, D. Blanquaert, S. Herman, L. Sedel and J. Witvoet, pp. 1203–1232.

Machinery's Handbook, by Erik Oberg, Franklin D. Jones, Holbrook L. Horton and Henry H. Ryffel, 24th Edition, 1992, "Standard Tapers", pp. 926–927.

"Industrial Belts and Sheaves", The Gates Rubber Company, 1988, pp. 14–15.

Mechanical Engineers' Handbook, Sixth Edition, 1958, "Metal–Cutting Tools and Machines" by O. W. Boston, pp. 13–56 through 13–57.

"Ceramic Cup Inserts for Hip Endoprostheses" by G. Willmann, H, Kalberer and H.–G. Pfaff, pp. 1–27, (English Translation and German article), prior to Nov. 7, 1997.

"Bulletin of the Hospital for Joint Diseases Orthopaedic Institute", vol. 49, No. 2, 1989, "Zirconia: The Second Generation of Ceramics for Total Hip Replacement", by Pascal Christel, pp. 170–177.

"Lord Madreporique", Rosenthal Biokeramik®, Howmedica GmbH, 4 pages, prior to Nov. 7, 1997.

The Journal of Bone and Joint Surgery, "Fixation of Hip Prostheses by Hydroxyapatite, Ceramic Coatings", R. J. Furlong, J. F. Osborn, British vol. 73–B, No. 5, Sep. 1991, pp. 741–745.

Acta Orthopaedica Belgica, vol. 59—Suppl. I—1993, "Six Years Use of the Unmodified Furlong Hydroxyapatite Ceramic Coated Total Hip Replacement", R. Furlong, 3 pages.

The Journal of Arthroplasty, vol. 11 No. 7, 1996, "Mittelmeier Ceramic–Ceramic Prosthesis after 10 years", Eduardo Garcia–Cimbrelo, MD, Jose–Manuel Martinez–Sayanes, MD, Alvaro Minuesa, MD, and Luis Munuera, MD, pp. 773–781.

Clinical Orthopaedics and Related Research, No. Two Hundred Thirty–Five, 1988 "Cementless Revisions of Failed Aseptic Cemented and Cementless Total Hip Arthroplasties. 284 Cases.", Gerald Lord, M.D., Jacques–Henri Marotte, M.D., Jean–Louis Guillamon, M.D. and Jean–Pierre Blanchard, M.D., pp. 67–74.

Biomaterials, Medical Devices, and Artificial Organs, an international journal, vol. 7, No. 1, 1979, "Development of a Ceramic Surface Replacement for the Hip. An Experimental Sialon Model.", Clarke, I.C., Phillips, W., McKellop, H., Coster, I.R., Hedley, A. and Amstutz, H.C., pp. 111–126.

"JRI Acetabular Cups", Joint Replacement Instrumentation, Ltd., 1 page, prior to Nov. 7, 1997.

Protesis Total de Cadera Furlong Recubierta de H–A.C., Joint Replacement Instrumentation, pp. 1–25, prior to Nov. 7, 1997.

Joint Replacement Instrumentation, "Hooded Inserts for Furlong® H–A.C. C.S.F. Cups", Instrumentation, Prostheses, 2 pages, 1993.

Machinery's Handbook, "Standard Tapers" by Erik Oberg, Franklin D. Jones, Holbrook L. Horton, 20th Edition, 1976, p. 1722.

Archives of Orthopaedic and Trauma Surgery, vol. III No. 5, Apr. 1992, "Prostaglandin $E_2$ Level in Tissue Surrounding Aseptic Failed Total Hips", L. Sedel, J. Simeon, A. Meunier, J.M. Villette and S.M. Launay, pp. 255–258.

Clinical Orthopaedics and Related Research, No. Two Hundred Ninety–Eight, 1994, "Alumina–Alumina Hip Replacement in Patients Younger than 50 Years Old", Laurent Sedel, Remy S. Nizard, Luc Kerboull, Jacques Witvoet, pp. 175–183.

Biological and Biomechanical Performance of Biomaterials, "Examination of Retrieved Hip–Prostheses: Wear of Alumina/Alumina Components", 1986, J.M. Dorlot, P. Christel, L. Sedel, J. Witvoet and P. Boutin, pp. 495–500.

Revue Du Rhumatisme, 57, No. 9, Oct. 1990, "La Prothese Totale De Hanche Avant 50 Ans", L. Sedel, P. Christel, L. Kerboull, J. Witvoet, pp. 605–611.

Clinical Orthopaedics and Related Research, No. Two Hundred Eighty–Two, Long–Term Effects of Alumina Components in Total Hip Prostheses, Jean–Marie Dorlot, Jan. 31, 1991, pp. 47–42.

Revue Du Chirurgie Orthopedique Et Reparatrice De L'appareil Moteur, vol. 79 No. 7, 1993, "Arthroplastie Totale De Hanche Avec Anneau Cotyloidien En Titane Visse", J. Witvoet, Z. Darman, P. Christel, F. Furmery.

Technique De Mise En Place D'Un Cotyle Sans Ciment Ceraver S.C., 7 Sheets, Prior to Nov. 7, 1997.

Annales Orthopediques De L'ouest, "Evolution De L'Arthroplastie Sans Ciment Avec Le Couple Alumine–Alumine Et L'Alliage De Titane (1971–1984)", P. Boutin, pp. 111–116, prior to Nov. 7, 1997.

Cahiers d'Enseignemeht de la SOFCOT, No. 10, 1979, "New Materials Used in Total Hip Replacement", P. Boutin, D. Blanquaert, pp. 27–44.

J. Biomed. Mater. Res.: Applied Biomaterials, vol. 23, No. A3, 299–310 (1989)"Wear Analysis of Retrtieved Alumina Heads and Sockets of Hip Prostheses", J. M. Dorlot, P. Christel and A. Meunier.

"La Prothese 'SC' Sans Ciment The 'SC' Cementless Prosthesis", 4 pages, prior to Nov. 7, 1997.

"Anatomiques" Osteal, 12 pages, "Les Protheses Qui Repartissent Et Transmettent Les Contrainates A L'os", prior to Nov. 7, 1997.

Photographs "A" of Ceraver Osteal Metal Acetabular Shell and Ceramic Insert (having self locking mating tapers) prior to Nov. 7, 1997.

Photographs "B" of Ceraver Osteal Acetabular Shell, Insert and Ball, prior to Nov. 7, 1997, 3 pages.

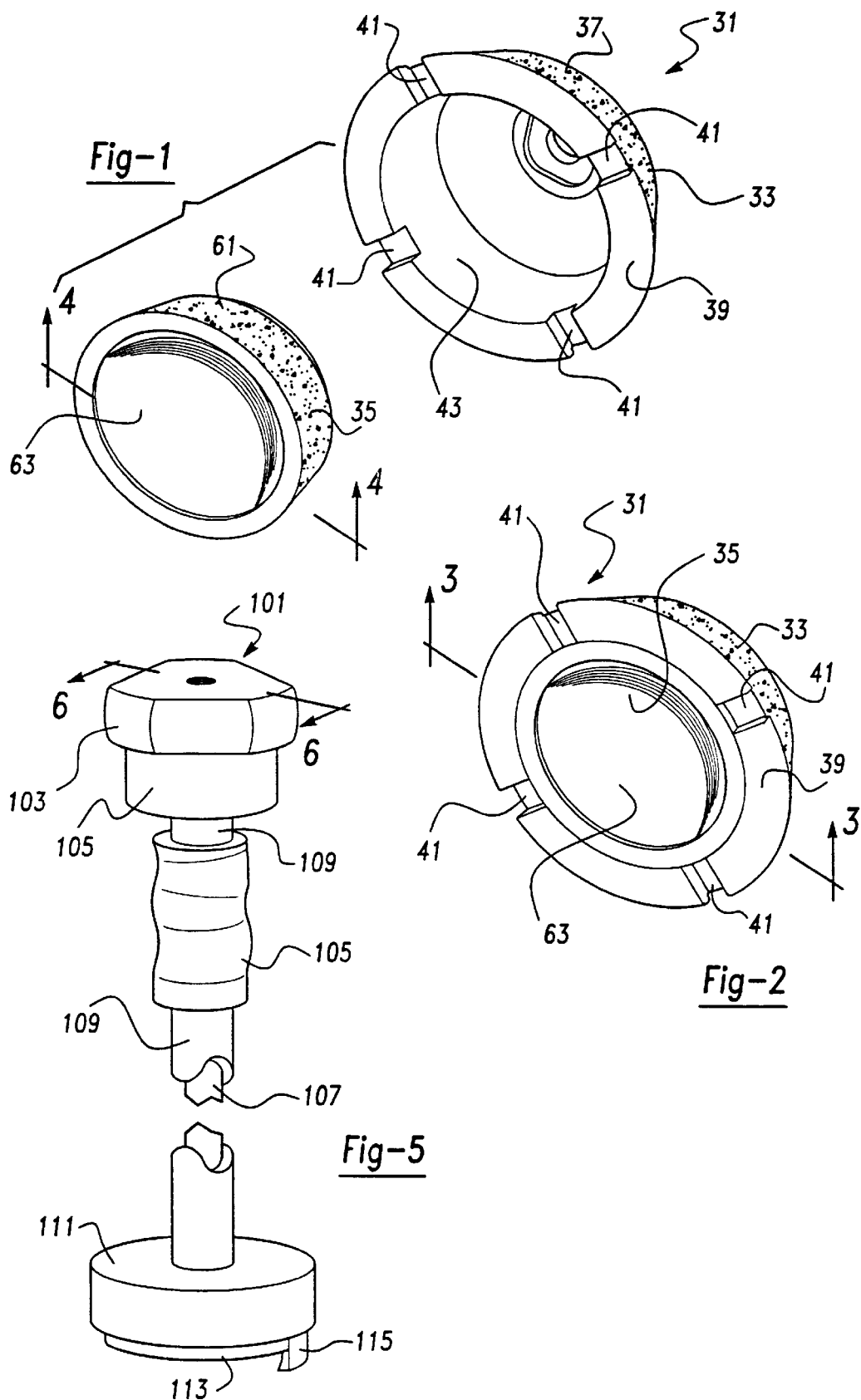

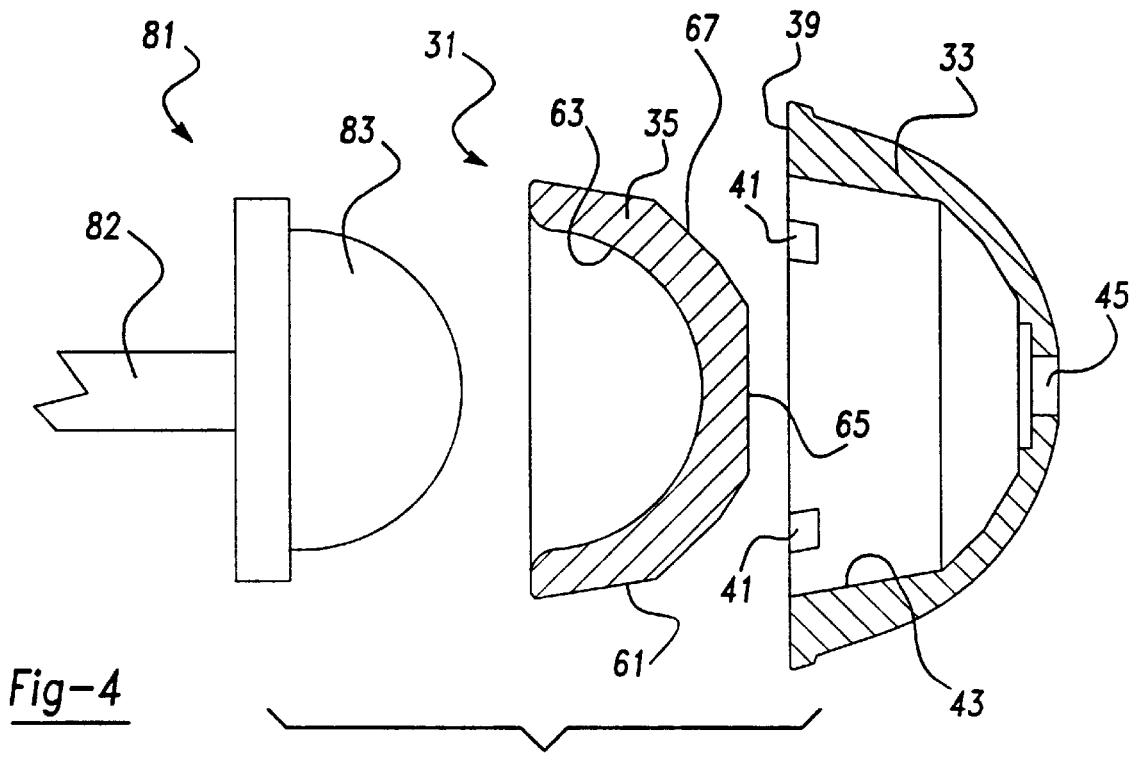
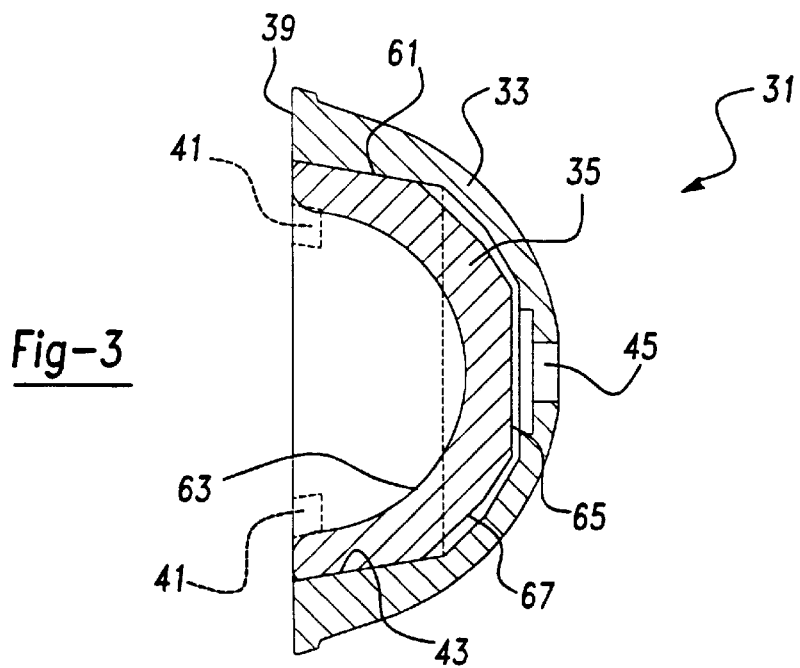

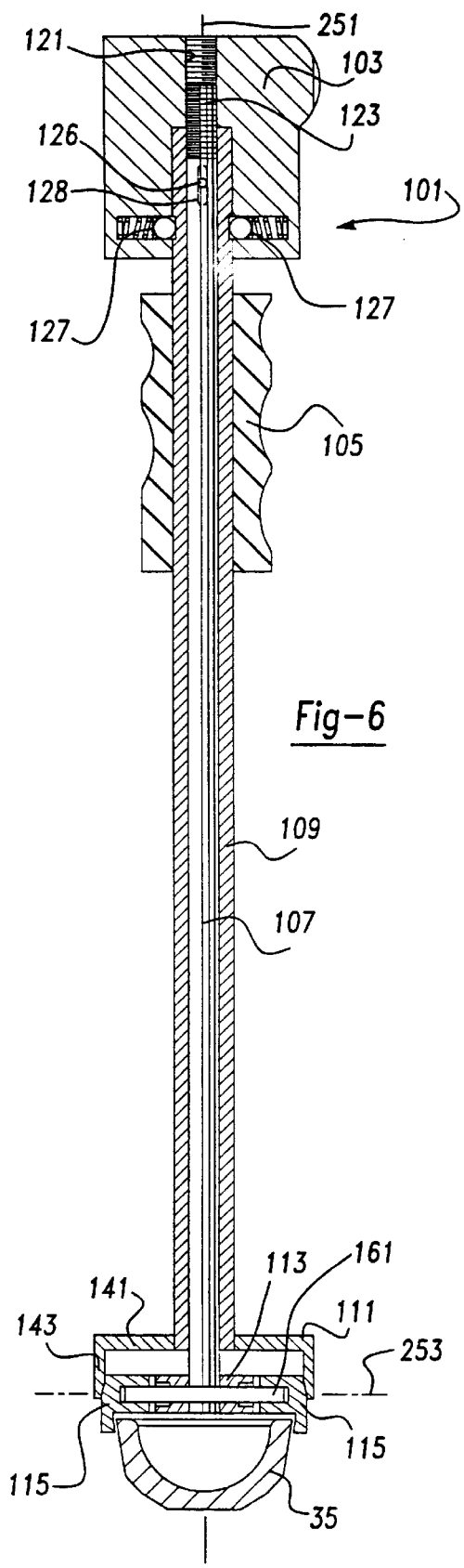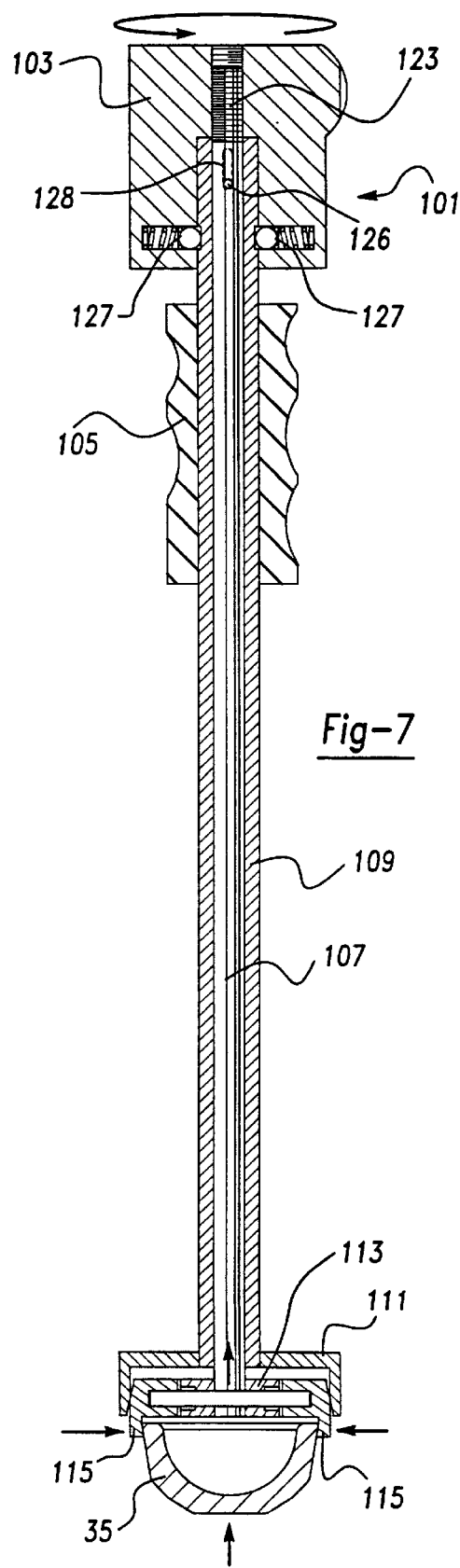

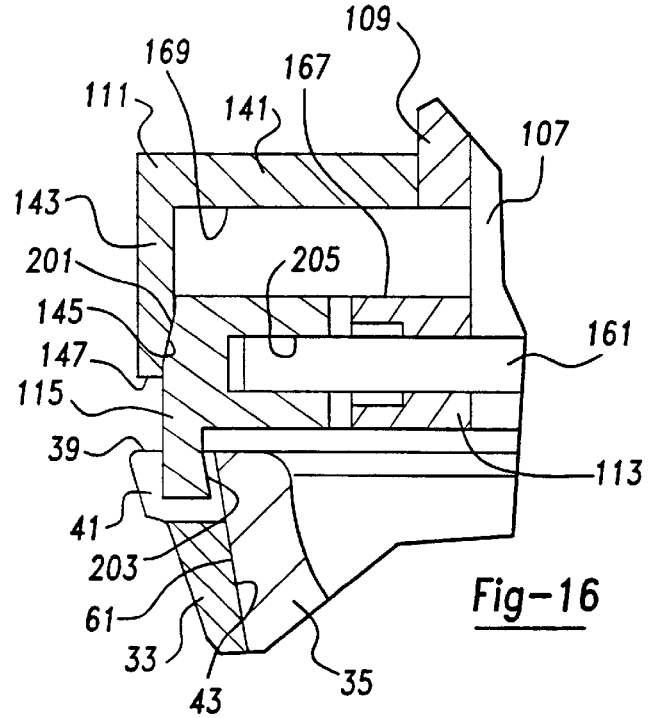

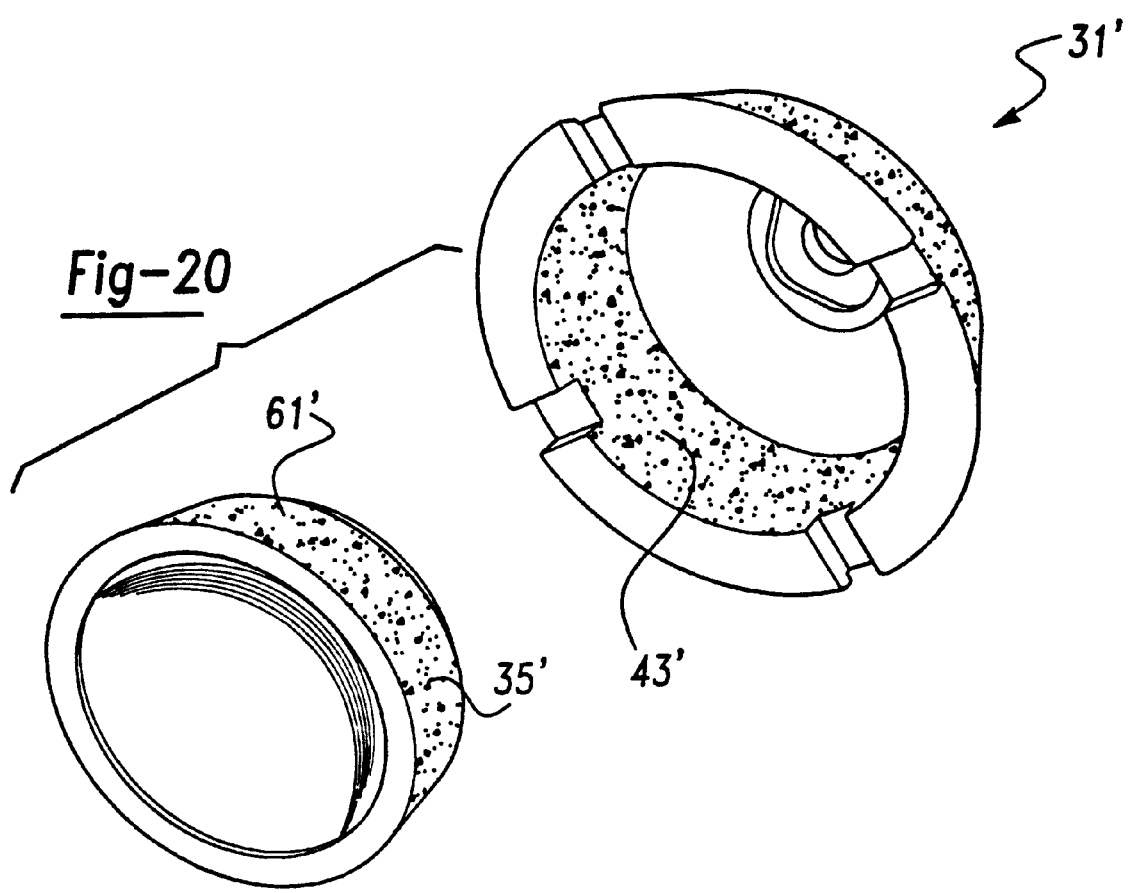

ACETABULAR LINER EXTRACTOR

BACKGROUND OF THE INVENTION

This invention relates generally to orthopedic prostheses and more specifically to an acetabular liner extractor for use with a prosthetic acetabular cup.

Ceramic-to-ceramic and metal-to-metal bearing surfaces have been commonly used in orthopedic prostheses. More specifically, first generation acetabular prosthetic devices were originally constructed with monoblock components. However, in the mid-1980's, modular inserts were introduced which employed a bearing surface made from one material while the portion in contact with the patient's bone was made from a dissimilar material. One such example used an alumina liner in a titanium shell. The alumina liner and titanium shell were connected by a self-locking Morse taper. Such tapered ceramic liner and titanium shell combinations are well known in the industry and have been sold since 1988 by Joint Replacement Instrumentation Ltd. as the FURLONG® H-A.C Screw-In Cup. Another well known ceramic liner and metal shell acetabular cup assembly, having self-locking tapered mating surfaces, was sold by Ceraver of France and disclosed in "The Use of Dense Alumina-Alumina Ceramic Combination in Total Hip Replacement," *Journal of Biomedical Materials Research*, Vol. 22, pages 1203–1232 (1988), authored by P. Boutin, P. Christel, J. Dorlot, A. Meunier, A. deroquancourt, D. Blanquaert, S. Herman, L. Sedel and J. Witvoet.

Various removal instruments have been employed in an effort to remove the liner from the shell. One such instrument was designed to slide down a thin cavity between the shell and liner and wedge the liner out from the back side. This instrument has enjoyed limited success as it is fairly small in cross-section and the force required to separate the shell and liner can deform or fracture the instrument without separating the components. Another instrument utilized a pipe-like member that rests against the shell without touching the liner; a hammer blow was then applied to the pipe-like member whereby the resonant frequency, vibration or impact force created in the shell loosens the taper connection.

Furthermore, U.S. Pat. Nos. 5,413,603 and 5,282,864 disclose a tapered liner and shell which incorporate set screws disposed in slots in the liner and shell which act against notches to disengage the locking taper. Other notches are employed for engagement by a tang of a loosening instrument to pry the liner from the shell. These slots and notches require additional machining of the liner and shell thereby increasing manufacturing costs and reducing the amount of contact area of the taper. Moreover, this off-center prying manner of removal causes bending forces between the liner and shell which appears to make disassembly somewhat difficult.

SUMMARY OF THE INVENTION

In accordance with the present invention, a preferred embodiment of an extractor employs a pair of arms which laterally move toward each other, thereby applying compressive forces against a first prosthetic component toward a longitudinal centerline. These compressive forces, in combination with longitudinal movement of the arms in relation to a collar of the extractor, serve to easily extract the liner from the shell. In a further aspect of the present invention, a handle of an extractor is rotated to move a pair of arms engaging a liner.

The present invention is advantageous over conventional devices due to the application of even and uniform compression and separation forces around the entire periphery of the liner. Furthermore, the extractor is very easy to use and quick. It is significant that no components are destroyed during extraction of the present invention liner. By employing rotational actuation to cause lateral and longitudinal arm-to-collar movement, the present invention extractor avoids the need for traditionally disadvantageous prying forces for component separation. No external liner grooves, notches, undercut channels or tabs, which are expensive to machine, are needed in the liner of the present invention. The construction of the present invention also allows for interchangeability of alternate liner materials, such as ceramic, without altering the design of the shell. Additional advantages and features of the present invention will become apparent from the following description and appended claims, taken in conjunction with the accompanying drawings.

BRIEF DESCRIPTION OF THE DRAWINGS

FIG. 1 is an exploded perspective view showing the preferred embodiment of a liner and shell of the present invention;

FIG. 2 is an assembled perspective view showing the preferred embodiment liner and shell;

FIG. 3 is a cross sectional view, taken along line 3—3 of FIG. 2, showing the preferred embodiment liner and shell;

FIG. 4 is an exploded and partially cross sectional view, taken along line 4—4 of FIG. 1, similar to that of FIG. 3, showing the preferred embodiment liner, shell and an insertion tool;

FIG. 5 is a perspective view showing the preferred embodiment extractor of the present invention;

FIGS. 6 and 7 are cross sectional views, taken along line 6—6 of FIG. 5, showing the preferred embodiment extractor relative to the liner and shell;

FIG. 13 is a side elevational view showing an inner shaft of the preferred embodiment extractor;

FIG. 14 is a side elevational view showing an arm of the preferred embodiment extractor;

FIG. 15 is a bottom elevational view showing the arm of the preferred embodiment extractor;

FIGS. 16–19 are enlarged and fragmentary cross sectional views, similar to that of FIG. 6, showing the preferred embodiment extractor in various operational positions relative to the liner and shell; and FIG. 20 is an exploded perspective view showing an alternate embodiment of the liner and shell.

DETAILED DESCRIPTION OF THE PREFERRED EMBODIMENT

Figure 8:
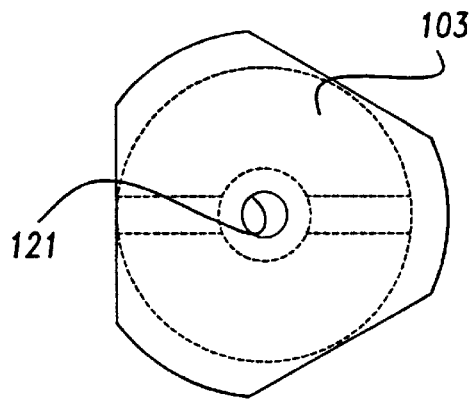
FIG. 8 is a top elevational view showing a handle of the preferred embodiment extractor.

The following discussion of the preferred embodiment of the present invention is merely exemplary in nature and is not intended to limit the invention or its application or uses.

Referring to FIGS. 1–3, the preferred embodiment of an acetabular prosthesis 31 includes a shell 33 and a liner 35. The shell 33 has a generally spherical exterior surface 37 with a roughened porous coating texture for engaging a patient's acetabulum. A circular and flat shoulder 39 of the shell 33 contains four depressions 41. An interior side surface 43 of the shell 33 is provided with an approximately 18 degree 55 minute included frusto-conical taper angle with a smooth finish. A single aperture 45 is disposed within a bottom of the shell 33 for allowing access of tools and visibility during surgery. However, the shell 33 does not contain any bone screw receiving holes. The shell 33 is preferably machined from a metallic material such as Ti-6Al-4V per ASTM F136.

The liner 35 has a frusto-conical tapered external side surface 61 of an approximately 18 degree 55 minute included angle, matching surface 43 of the shell 33. A fine sand blasting is applied to the external side surface 61 to achieve a sufficient mechanical interlock with the interior side surface 43 of the shell 33. FIG. 20 shows an alternate embodiment wherein an interior side surface 43' of a shell 33' is also roughened by a fine sand blasting to further mechanically interlock, with an exterior side surface 61' of a liner 35'. Referring again to the preferred embodiment of FIGS. 1–3, it is believed that angles greater than 18° are necessary to achieve proper removal of the liner 35 from the shell 33 using the tools disclosed herein. An interior partially spherical surface 63 of the liner 35 is highly polished for receiving a ball-like head of a femur prosthesis. This interior surface 63 is machined, ground and then polished. A flat bottom surface 65 of the liner 35 and an intermediate external surface 67 of the liner 35 are positioned adjacent to the tapered external side surface 61. The liner 35 is preferably made from Co-Cr-Mo metallic alloy, per ASTM F1537. However, it is alternately envisioned that a ceramic liner of similar shape can be used with the preferred embodiment shell.

As can be observed in FIGS. 3 and 4, an insertion tool 81 is employed to assemble the liner 35 in the shell 33. The insertion tool 81 includes a metallic shaft 82 and a rubber head 83. When a surgeon strikes an end of the shaft 82, the head 83 will force the liner 35 into the shell 33 such that the mating surfaces 43 and 61 will mechanically interlock and engage each other so as to securely retain the liner 35 in the shell 33. Since the surfaces 43 and 61 are not interrupted by any grooves or other significant discontinuities, the surface 43 will contact against the surface 61 in a continuous circumferential manner thereby minimizing any localized stresses between the components. However, there is a slight gap between the surfaces 65 and 67 of the liner and the adjacent bottom surfaces of the shell 33 when assembled. This gap serves to minimize costly precision machining tolerances and the potential for undesired interference in these areas.

Figure 9:
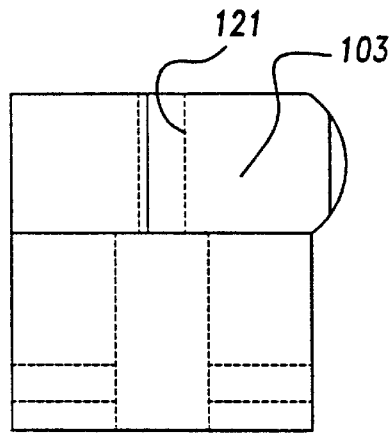
FIG. 9 is a side elevational view showing the handle of the preferred embodiment extractor.
Figure 10:
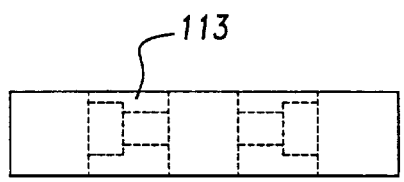
FIG. 10 is a side elevational view showing an intermediate plate of the preferred embodiment extractor.
Figure 11:
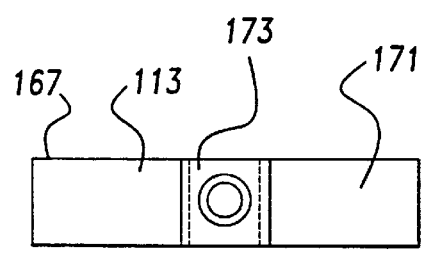
FIG. 11 is a side elevational view, taken 90° from that of FIG. 10, showing the intermediate plate of the preferred embodiment extractor.
Figure 12:
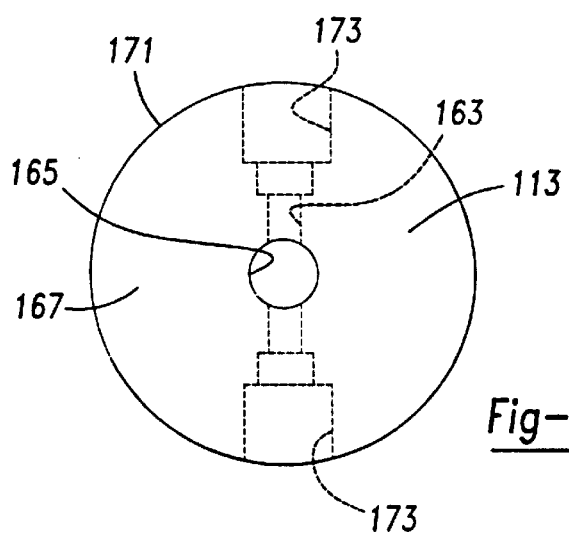
FIG. 12 is a top elevational view showing the intermediate plate of the preferred embodiment extractor.

Referring now to FIGS. 5–16, a preferred embodiment extractor 101 includes a rotatable knob-like handle 103, a gripping support 105, an inner shaft 107, an outer shaft 109, a collar 111, an intermediate plate 113 and a pair of arms 115. The handle 103 has a generally triangular top configuration with rounded corners joined to a lower body and is suitable for being gripped by the surgeon. A pair of compression spring loaded ball detents 127 disposed in the body of the handle 103 engage a peripheral groove in the outer shaft 109. A central bore 121 is internally threaded for receiving an externally threaded segment 123 at a proximal end 125 of the inner shaft 107. A pin 126 extends between a hole in the inner shaft 107 and a longitudinally elongated slot 128 and the outer shaft 109 to prevent relative rotation but allows relative longitudinal movement. The plastic gripping support 105 is stationarily affixed to the outer shaft 109 by way of a heated pressfit over a knurled surface on the outer shaft 109.

A laterally extending wall 141 of the collar 111 is stationarily joined to outer shaft 109 by welding, a pressfit or the like. A circular-cylindrical, longitudinally extending wall 143 depends from the periphery of the laterally extending wall 141 and has a generally frusto-conical internal surface 145 adjacent to an end 147.

The inner shaft 107 extends centrally through the collar 111 and is located to the intermediate plate 113 by an elongated, cylindrical pin 161 and welded. The pin 161 is received within a laterally extending tunnel 163 of the intermediate plate 113 and spans across a central orifice 165 which receives the inner shaft 107. An enlarged flat surface 167 of the intermediate plate 113 faces a corresponding flat surface 169 of the collar 111. A generally circular-cylindrical peripheral surface 171 borders the flat surface 167 and has a pair of notches 173 for receiving the arms 115.

Each arm 115 has a chamfered external surface 201 which movably rides along the frusto-conical surface 145 of the collar 111. A reverse tapered interior surface 203 of each arm 115 has an angle similar to that of the tapered side surface 61 of the liner 35. An internal passageway 205 in each arm 115 movably receives an end of the pin 161. The extractor components are all made from 455, 17-4 or 304 stainless steel or the like.

Figure 17:
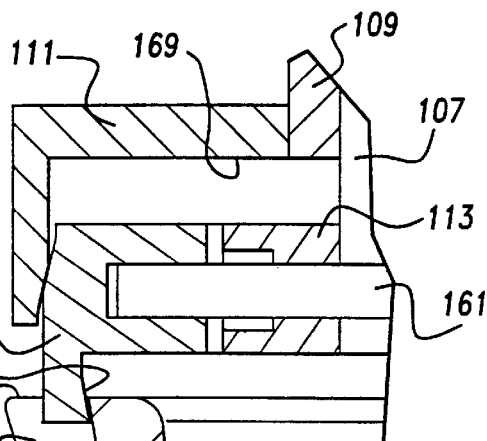
Figure 18:
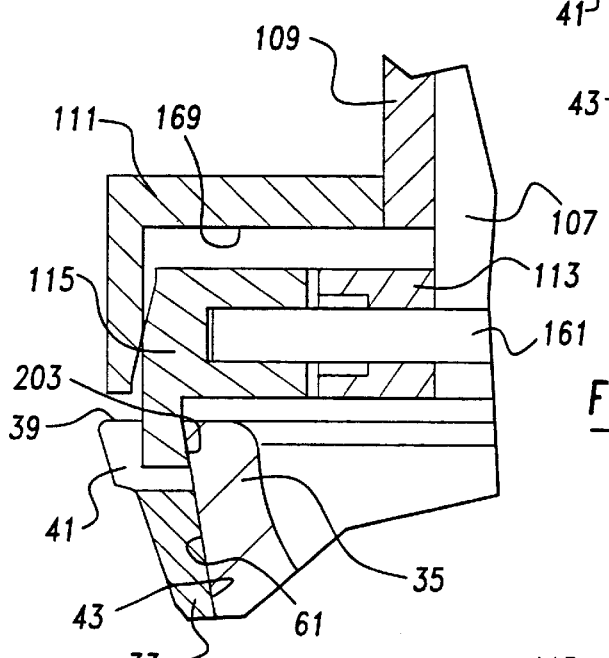
Figure 19:
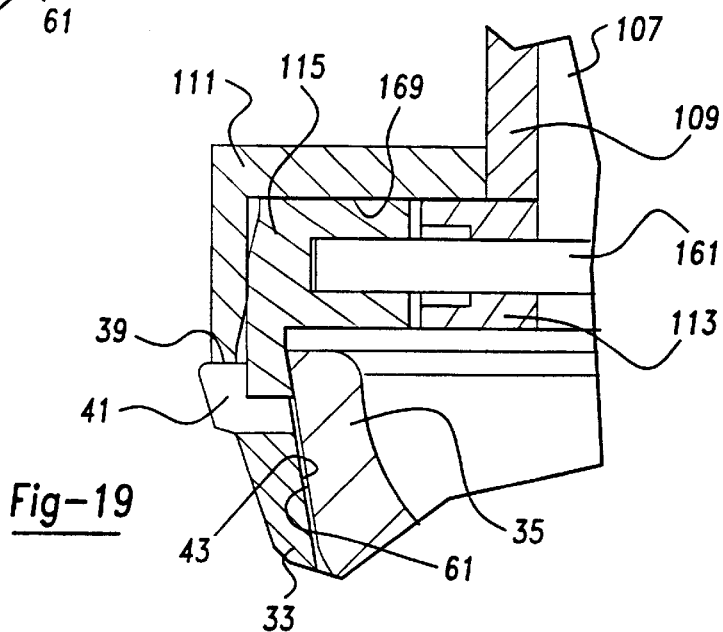

The function of the extractor 101 can be viewed with reference to FIGS. 6, 7 and 16–19. When the surgeon rotates the handle 103 relative to the gripping support 105, the outer shaft 109, the collar 111 and the threaded bore 121 will remain stationary but will cause the inner shaft 107 to move toward the handle along a longitudinal axis 251, as can be observed by comparing FIGS. 6 and 7. The longitudinal movement of the inner shaft 107 will coincidentally cause the intermediate plate 113 to longitudinally move toward the collar 111. Since the arms 115 will longitudinally move with the intermediate plate 113, the arms 115 will be pulled into the collar 111 such that the frusto-conical surface 145 of the collar 111 will simultaneously push the chamfered surface 201 of each arm 115 along a lateral axis 253 toward the longitudinal centerline 251.

Accordingly, FIGS. 16–19 illustrate the generally simultaneous and uniform lateral compression and longitudinal extraction of the liner 35 from the shell 33. The arms 115 are first inserted into two of the four depressions 41 in the shell 33. Next, upon rotation of the handle, the arms 115 are laterally moved toward each other to close a gap bordering the liner 35 until they laterally and evenly abut against the tapered surface 61 of the liner 35. Concurrently, as the arms 115 are advanced toward each other and toward the surface 169 of the collar 111, the end 147 of the collar 111 abuts against the shoulder 39 of the shell 33. As the handle is further rotated, the arms 115 laterally apply compressive forces against the liner 35 simultaneous with the collar 111 longitudinally pulling the liner 35 from the shell 33. This provides for an even and peripherally uniform load distribution upon the shell 33 so as to uniformly alleviate pressure and remove the liner 35 from the shell 33. This extraction is done in a strictly longitudinal direction without the need for a prying or torquing action which reduces the chance of undesired removal of the shell 33 from the acetabulum while this extraction is occurring.

While the preferred embodiments of the present invention acetabular liner extractor have been described herein, it will be appreciated that other constructions can be provided. For example, the extractor of the present invention can be used with other prosthesis constructions. Furthermore, the specific disclosed shapes of the handle, support, collar, intermediate plate and arms may be varied as long as the arms serve to apply laterally compressive forces against the liner and the device longitudinally pulls the liner out of the shell. It is also envisioned that the liner may extend beyond the shoulder of the shell such that the shell depressions are not needed. Additional arms may also be employed. Moreover, radial threads, screw holes or the like may be provided on the exterior portion of the shell. Various materials have been disclosed in an exemplary fashion, however, other materials may of course be employed. It is intended by the following claims to cover these and any other departures from the disclosed embodiments which fall within the true spirit of this invention.

What is claimed is:

1. In combination, an acetabular prosthetic apparatus and an extractor,
   (a) the acetabular prosthetic apparatus comprising:
      a shell having an exterior surface adapted to engage an acetabulum and an interior surface;
      a liner having a partially spherical interior surface operable to receive a ball, an exterior surface of said liner engaging said interior surface of said shell, said liner being secured in said shell;
   (b) the extractor comprising:
      a first arm;
      a second arm, said arms having engagement sections;
      a collar located adjacent to said arms, said collar having a projecting edge;
      a first shaft extending through said collar and being coupled to said arms;
      said arms operably moving toward and away from each other when said shaft is respectively moved in a first direction and a second direction concurrently with said arms operably moving toward and away from said collar, said first direction being opposite of said second direction; and
      a substantially flat shoulder of said shell having multiple depressions;
   (c) said projecting edge of said collar abutting against said shoulder of said shell concurrently with said engagement sections of said arms being received in said multiple depressions of said shell whereby said arms are provided access to said liner; and
   said arms of said extractor engaging and applying inwardly compressive forces against said liner when said shaft is moved in said first direction, said collar contacting against a portion of said shell and allowing said arms to longitudinally pull said liner out of said shell when said shaft is moved in said first direction.

2. The extractor of claim 1 further comprising an outer shaft concentrically surrounding said first shaft, said outer shaft being secured to said collar, said first shaft moving relative to said outer shaft.

3. The extractor of claim 2 further comprising a handle coupled to said shafts, movement of said handle causing movement of said first shaft and said arms.

4. The extractor of claim 1 further comprising an intermediate plate coupled to said first shaft, said arms being oppositely and movably coupled to said intermediate plate, said arms moving toward a longitudinal centerline of said first shaft when said first shaft moves in said first direction.

5. The extractor of claim 4 further comprising an enlarged flat surface of said intermediate plate facing a flat surface of said collar, a circular-cylindrical peripheral surface of said intermediate plate located in a corresponding circular-cylindrical interior surface of said collar, first and second notches located in said peripheral surface of said intermediate plate receiving said first and second arms, respectively.

6. The extractor of claim 1 wherein said collar includes:
   a wall laterally extending relative to said first shaft;
   a substantially cylindrical wall depending from said laterally extending wall being coaxially aligned with said first shaft; and
   a frusto-conical surface of said substantially cylindrical wall pointing away from said laterally extending wall.

7. The extractor of claim 6 further comprising a chamfered external surface located on each of said arms, said chamfered surface movably riding along said frusto-conical surface of said collar whereby said arms are moved laterally toward and away from each other when said arms are moved in a longitudinal direction relative to said collar, said longitudinal direction being substantially defined by an elongated axis of said first shaft, and a prosthetic engaging section located on internal surfaces of said arms which face each other.

8. The extractor of claim 1 wherein said arms simultaneously move linearly toward each other and longitudinally toward a gripping portion of said first shaft when said first shaft is rotated in relation to said collar.

9. In combination, an acetabular prosthetic apparatus and an extractor,
   (a) the acetabular prosthetic apparatus comprising:
      a shell having an exterior surface adapted to engage an acetabulum and an interior surface;
      a liner having a partially spherical interior surface for receiving a ball, an exterior surface of said liner engaging said interior surface of said shell, said liner being secured in said shell;
   (b) the extractor comprising:
      a first arm;
      a second arm;
      a collar located adjacent to said arms; and
      a first shaft extending through said collar and being coupled to said arms;
      said arms operably moving toward and away from each other when said shaft is respectively moved in a first direction and a second direction concurrently with said arms operably moving toward and away from said collar, said first direction being opposite of said second direction;
   (c) said arms of said extractor engaging and applying inwardly compressive forces against said liner when said shaft is moved in said first direction, said collar contacting against a portion of said shell and allowing said arms to longitudinally pull said liner out of said shell when said shaft is moved in said first direction.

10. The combination of claim 9 further comprising an outer shaft concentrically surrounding said first shaft, said outer shaft being secured to said collar, said first shaft moving relative to said outer shaft.

11. The combination of claim 10 further comprising a handle coupled to at least one of said shafts, rotational movement of said handle causing movement of said first shaft and said arms.

12. The combination of claim 9 further comprising an intermediate plate coupled to said first shaft, said arms being oppositely and movably coupled to said intermediate plate, said arms moving toward a longitudinal centerline of said first shaft when said first shaft moves in said first direction.

13. The combination of claim 12 further comprising an enlarged flat surface of said intermediate plate facing a flat surface of said collar, a circular-cylindrical peripheral surface of said intermediate plate located in a corresponding circular-cylindrical interior surface of said collar, first and second notches located in said peripheral surface of said intermediate plate receiving said first and second arms, respectively.

14. The combination extractor of claim 9 wherein said collar includes:
   a wall laterally extending from a longitudinal axis which is defined by said first shaft;
   a substantially cylindrical wall depending from said laterally extending wall being coaxially aligned with said first shaft; and
   a frusto-conical surface of said substantially cylindrical wall pointing away from said laterally extending wall.

15. The combination extractor of claim 14 further comprising a chamfered external surface located on each of said arms, said chamfered surface movably riding along said frusto-conical surface of said collar whereby said arms are moved laterally toward and away from each other when said arms are moved longitudinally toward and away from said laterally extending wall of said collar, a prosthetic engaging section located on internal surfaces of said arms which face each other.

16. The combination of claim 9 wherein said shell and said liner are metal.

17. In combination, an acetabular prosthetic apparatus and an extractor,
   (a) the acetabular prosthetic apparatus comprising:
      a shell having an exterior surface adapted to engage an acetabulum and a n interior surface;
      a liner having a partially spherical interior surface for receiving a ball, an exterior surface of said liner engaging said interior surface of said shell for securing said liner in said shell;
   (b) the extractor comprising:
      a first arm;
      a second arm; and
      a collar located adjacent to said arms, said collar being operable to contact said shell;
      said arms being movable relative to said collar, said arms operably engaging and applying compressive forces against said liner.

18. The combination of claim 17 wherein said exterior surface of said liner is roughened to provide a mechanical interlock with said interior surface of said shell.

19. The combination of claim 18 wherein said interior surface of said shell is roughened.

20. The combination of claim 19 further comprising reverse tapered interior surfaces of said arms engaging said exterior surface of said liner, said exterior surface of said liner having a taper.

21. The combination of claim 19 further comprising a substantially flat shoulder of said shell having multiple depressions, a projecting edge of said collar abutting against said shoulder of said shell concurrently with engagement sections of said arms being received in said multiple depressions of said shell whereby said arms are provided access to said liner.

22. The combination of claim 19 wherein said liner contacts against said shell in a continuous circumferential manner without any interruption of grooves.

23. The combination of claim 17 further comprising a member coupled to said arms, said member being rotatable to cause linear movement of said arms.

* * * * *

UNITED STATES PATENT AND TRADEMARK OFFICE
CERTIFICATE OF CORRECTION

PATENT NO. : 6,132,469
DATED : October 17, 2000
INVENTOR(S) : David W. Schroeder Page 1 of 1

It is certified that error appears in the above-identified patent and that said Letters Patent is hereby corrected as shown below:

Title page,
Item [56], Reference Cited,
"4,172,529" should be -- 4,172,296 --.

Item [56], Reference Cited, OTHER PUBLICATIONS,
"Role" should be -- Role -- and "Bearings" should be -- Bearings" -- (insert quotation marks). "Long" should be -- "Long -- and "Prostheses" should be -- Prostheses" -- (insert quotation marks), and "Retrieved" should be -- Retrieved --.

Item [56], Reference Cited, Foreign Application Data,
Add -- 16034-00  4/1992  Benelux --

Column 1,
Line 11, "1980's" should be -- 1980s --.

Signed and Sealed this

Thirtieth Day of April, 2002

Attest:

Attesting Officer

JAMES E. ROGAN
*Director of the United States Patent and Trademark Office*